United States Patent
Bourquin et al.

(10) Patent No.: US 12,126,918 B2
(45) Date of Patent: Oct. 22, 2024

(54) DETERMINING PIXEL INFORMATION

(71) Applicant: KONINKLIJKE PHILIPS N.V., Eindhoven (NL)

(72) Inventors: Yannyk Parulian Julian Bourquin, Eindhoven (NL); Jonathan Alambra Palero, Noord-Brabant (NL); Mathivanan Damodaran, S-Hertogenbosch (NL); Rieko Verhagen, Vught (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 129 days.

(21) Appl. No.: 17/928,973

(22) PCT Filed: Jun. 3, 2021

(86) PCT No.: PCT/EP2021/064899
§ 371 (c)(1),
(2) Date: Dec. 1, 2022

(87) PCT Pub. No.: WO2021/249857
PCT Pub. Date: Dec. 16, 2021

(65) Prior Publication Data
US 2023/0353889 A1    Nov. 2, 2023

(30) Foreign Application Priority Data

Jun. 10, 2020  (EP) .................................. 20179148

(51) Int. Cl.
*H04N 23/951* (2023.01)
*H04N 23/45* (2023.01)
(Continued)

(52) U.S. Cl.
CPC ........... *H04N 23/951* (2023.01); *H04N 23/45* (2023.01); *H04N 23/56* (2023.01); *H04N 23/74* (2023.01)

(58) Field of Classification Search
CPC ...... H04N 23/951; H04N 23/45; H04N 23/56; H04N 23/74; A61B 5/0077; A61B 5/441; A61B 5/6898
See application file for complete search history.

(56) References Cited

U.S. PATENT DOCUMENTS

2010/0149372 A1   6/2010 Silverstein
2011/0310376 A1*  12/2011 Shim .................... G01S 17/894
                                         356/4.07
(Continued)

FOREIGN PATENT DOCUMENTS

CN     108225217 A    6/2018
WO     2013171612 A1  11/2013
(Continued)

OTHER PUBLICATIONS

International Search Report and Written Opinion of PCT/EP2021/064899, dated Sep. 8, 2021.
(Continued)

*Primary Examiner* — Padma Haliyur

(57) ABSTRACT

In an embodiment, a method (100) is described. The method is a computer-implemented method. The method comprises receiving (102) pixel information corresponding to at least part of a first, second and third image, acquired by an imaging system, of a subject illuminated by temporally modulated illumination. A time delay between an acquisition start time of the first, second and third images is such that there is an overlap in time during acquisition of the first, second and third images. The method further comprises determining (104) modified pixel information for constructing a modified image of the subject. The modified pixel
(Continued)

information is determined based on: a difference between the received pixel information of the first, second and third images to reduce an effect of ambient lighting in the received pixel information; and a combination of the received pixel information to cancel out a spatial intensity modulation pattern apparent in each of the first, second and third images. The spatial intensity modulation pattern is due to a timing relationship between an imaging time period over which the imaging system acquires each image and a modulation time period of the temporally modulated illumination.

15 Claims, 5 Drawing Sheets

(51) Int. Cl.
*H04N 23/56* (2023.01)
*H04N 23/74* (2023.01)

(56) References Cited

U.S. PATENT DOCUMENTS

| | | |
|---|---|---|
| 2012/0016892 A1 | 1/2012 | Wang |
| 2012/0194698 A1 | 8/2012 | Cami |
| 2014/0218556 A1* | 8/2014 | Chen ................... H04N 23/73 348/222.1 |
| 2015/0035949 A1 | 2/2015 | Rouh |
| 2015/0215547 A1 | 7/2015 | Muller |
| 2015/0249496 A1 | 9/2015 | Muijs |
| 2018/0168454 A1 | 6/2018 | Ando |
| 2020/0154024 A1 | 5/2020 | Watson |
| 2020/0341126 A1* | 10/2020 | Yates ................... G01S 7/4816 |
| 2021/0335009 A1* | 10/2021 | Kao ....................... G06T 7/80 |

FOREIGN PATENT DOCUMENTS

| | | |
|---|---|---|
| WO | 2018001727 A1 | 1/2018 |
| WO | 2021089422 A1 | 5/2021 |
| WO | 2021165035 A1 | 8/2021 |

OTHER PUBLICATIONS

Vizireanu, Dragos Nicolae et al, "Analytical formula for three points sinusoidal signals amplitude estimation errors," International Journal of Electronics, vol. 99,. No. 1, Jan. 2012, pp. 149-151.

Vizireanu, Dragos Nicolae et al "Single sine wave parameters estimation method based on four equally spaced samples," International Journal of Electronics, vol. 98,. No. 7, Jul. 2011, pp. 941-948.

* cited by examiner

DETERMINING PIXEL INFORMATION

CROSS-REFERENCE TO PRIOR APPLICATIONS

This application is the U.S. National Phase application under 35 U.S.C. § 371 of International Application No. PCT/EP2021/064899, filed on Jun. 3, 2021, which claims the benefit of European Patent Application No. 20179148.0, filed on Jun. 10, 2020. These applications are hereby incorporated by reference herein.

FIELD OF THE INVENTION

The invention relates to a method, apparatus and tangible machine-readable medium for use in imaging in certain settings.

BACKGROUND OF THE INVENTION

A topic of interest in the field of non-obtrusive measurement and monitoring relates to skin sensing for personal care and health applications. Skin sensing systems are being developed that promise skin quantification and monitoring of features in the skin that may offer users information that is too small to detect, too faint to notice or too slow to follow. To deliver results that are acceptable to users, such skin sensing systems may need to provide sensitivity and specificity when performing skin sensing. Providing measurements taken by such skin sensing systems are proven to be robust and reliable, users may establish trust in these skin sensing systems.

Imaging-based skin sensing systems may need to determine information that could be affected by difficult-to-control parameters such as variations in ambient lighting. For example, certain uncontrolled environments such as at a user's home may feature undefined and/or potentially varying ambient lighting. Such uncontrolled environments may lead to erroneous measurements of a user's skin, which may, in turn, lead to unacceptable or untrusted results for the user. The imaging performance of some cameras (such as smartphone cameras) used in some imaging-based skin sensing systems may be variable such that the imaging data is unpredictable or unreliable.

Imaging-based skin sensing systems may implement various image processing techniques in order to determine certain information about the user's skin and/or the ambient lighting conditions. Relative motion between a user and an imaging system may cause errors when implementing certain image processing techniques.

SUMMARY OF THE INVENTION

Aspects or embodiments described herein relate to improving imaging in certain settings. Aspects or embodiments described herein may obviate one or more problems associated with certain image processing techniques where there is relative motion between a subject (e.g., user) and an imaging system.

In a first aspect, a method is described. The method is a computer-implemented method. The method comprises receiving pixel information corresponding to at least part of a first, second and third image of a subject illuminated by temporally modulated illumination. The first, second and third images are acquired by an imaging system. A time delay between an acquisition start time of the first, second and third images is such that there is an overlap in time during acquisition of the first, second and third images. The method further comprises determining modified pixel information for constructing a modified image of the subject. The determined modified pixel information is based on a difference between the received pixel information of the first, second and third images to reduce an effect of ambient lighting in the received pixel information. The determined modified pixel information is further based on a combination of the received pixel information to cancel out a spatial intensity modulation pattern apparent in each of the first, second and third images. The spatial intensity modulation pattern is due to a timing relationship between an imaging time period over which the imaging system acquires each image and a modulation time period of the temporally modulated illumination.

Some embodiments relating to the first aspect are described below.

In some embodiments, the time delay between the acquisition start times of the first, second and third images is based on the modulation time period of the temporally modulated illumination. The time delay between the acquisition start times may correspond to the modulation time period divided by the number of the images.

In some embodiments, the imaging system comprises at least two imaging devices for acquiring the first, second and third images.

In some embodiments, one of the imaging devices is used to acquire at least one of the first, second and third images and at least one other of the imaging devices is used to acquire at least one other of the first, second and third images.

In some embodiments, the method further comprises causing the imaging system to acquire the first, second and third images.

In some embodiments, the method further comprises: receiving an indication of a modulation parameter of the temporally modulation illumination; determining an operating parameter for the imaging system based on the indication; and causing the imaging system to operate according to the operating parameter.

In some embodiments, a modulation frequency of the temporally modulated illumination and/or a frame rate associated with the first, second and third images is configured such that a phase shift between the spatial intensity modulation patterns of the first, second and third images is the same.

In some embodiments, the method further comprises, before determining the modified pixel information, identifying whether or not a position of the subject within the first, second and third images is the same. Where a difference in the subject's position in at least one of the images compared with at least one other of the images exceeds a threshold, the method further comprises implementing an image shift operation in at least one of the first, second and third images so that the position of the subject in each of the first, second and third images is the same.

In some embodiments, the modified pixel information for constructing the modified image of the subject is determined by subtracting pixel information of different pair combinations of the first, second and third images to reduce the effect of ambient lighting in the received pixel information and combining the received pixel information to cancel out the spatial intensity modulation pattern apparent in each of the first, second and third images.

In some embodiments, the imaging system is configured to operate in a mode according to the timing relationship between the imaging time period over which the imaging system acquires each image and the modulation time period of the temporally modulated illumination, wherein the mode is: a rolling shutter mode where the imaging time period of the imaging system is longer than the modulation time period; or a global shutter mode where the imaging time period is shorter than the modulation time period.

In some embodiments, receiving the data further comprises receiving pixel information corresponding to at least part of at least one additional image of the subject, wherein the time delay between the acquisition start time of the first, second, third and at least one additional image is such that there is an overlap in time during acquisition of the first, second, third and the at least one additional image. The modified pixel information is determined based on: a difference between the received pixel information of the first, second, third and at least one additional images to reduce an effect of ambient lighting in the received pixel information; and a combination of the received pixel information to cancel out a spatial intensity modulation pattern apparent in each of the first, second, third and at least one additional images.

In a second aspect, a tangible machine-readable medium is described. The tangible machine-readable medium stores instructions which, when executed by at least one processor, cause the at least one processor to implement the method according to the first aspect or any related embodiment.

In a third aspect, apparatus is described. The apparatus comprises processing circuitry. The processing circuitry comprises a receiving module and a determining module. The receiving module is configured to receive pixel information corresponding to at least part of a first, second and third image of a subject illuminated by temporally modulated illumination. The first, second and third images are acquired by an imaging system. A time delay between an acquisition start time of the first, second and third images is such that there is an overlap in time during acquisition of the first, second and third images. The determining module is configured to determine modified pixel information for constructing a modified image of the subject. The determined modified pixel information is based on a difference between the received pixel information of the first, second and third images to reduce an effect of ambient lighting in the received pixel information. The determined modified pixel information is further based on a combination of the received pixel information to cancel out a spatial intensity modulation pattern apparent in each of the first, second and third images. The spatial intensity modulation pattern is due to a timing relationship between an imaging time period over which the imaging system acquires each image and a modulation time period of the temporally modulated illumination.

Some embodiments relating to the third aspect are described below.

In some embodiments, the apparatus further comprises: the imaging system for acquiring the pixel information corresponding to at least part of the first, second and third images; and/or an illumination unit for providing the temporally modulated illumination.

In some embodiments, the imaging system comprises at least two imaging devices. The imaging system may be configured to operate in a mode according to the timing relationship between the imaging time period over which the imaging system acquires each image and the modulation time period of the temporally modulated illumination. The mode is: a rolling shutter mode where the imaging time period of the imaging system is longer than the modulation time period; or a global shutter mode where the imaging time period is shorter than the modulation time period.

These and other aspects of the invention will be apparent from and elucidated with reference to the embodiment(s) described hereinafter.

BRIEF DESCRIPTION OF THE DRAWINGS

Exemplary embodiments of the invention will now be described, by way of example only, with reference to the following drawings, in which.

DETAILED DESCRIPTION OF THE EMBODIMENTS

In certain settings, ambient lighting may affect the performance of certain imaging-based skin sensing systems. Images acquired by an imaging system may suffer from artefacts caused by relative motion between a subject and the imaging system. This relative motion may be due to the subject not being able to easily stay in the same position and/or due to the subject holding a device comprising the imaging system and therefore the subject may find it difficult to keep the imaging system steady. Examples of the device include a smart device such as a smartphone, tablet, smart mirror or any other device capable of displaying an image or a representation of an image of the subject.

This relative motion may mean that a consecutive set of images of the subject may show the subject in different positions within the image frames and/or distort the appearance of the subject in the set of images. Embodiments described herein may therefore provide a way to reduce an effect of this relative motion when performing certain image processing techniques such as ambient lighting correction, normalization and/or reduction of an effect of ambient lighting variation between consecutive images.

Figure 1:
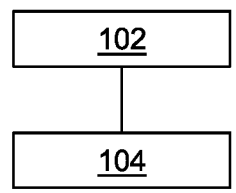
FIG. 1 refers to a method of improving imaging in certain settings according to an embodiment.

FIG. 1 shows a method 100 (e.g., a computer-implemented method) of improving imaging in certain settings. The method 100 may be implemented by a computer such as a user device, or a server or cloud-based service (e.g., communicatively coupled to the user device).

The method 100 comprises, at block 102, receiving pixel information (e.g., 'data' or 'intensity data' such as pixel intensity values) corresponding to at least part of a first, second and third image, acquired by an imaging system, of a subject illuminated by temporally modulated illumination. A time delay between an acquisition start time of the first, second and third images is such that there is an overlap in time during acquisition of the first, second and third images.

During image acquisition (e.g., by an imaging system as described in more detail below) of the first, second and third images, part of these images may be received by the computer implementing this method 100. For example, in an embodiment where the images are acquired by an imaging system configured to operate in a rolling shutter mode, part of the image may be acquired and sent to the computer for processing before a subsequent part of the image is acquired and sent to the computer. In other similar words, an entire image frame does not need to be acquired in order to facilitate implementation of the rest of the method 100. However, in some cases, the entire images may be acquired before implementing the rest of the method 100.

An illumination unit, as will be described in more detail below, provides the temporally modulated illumination. The illumination unit may or may not be controlled by the same computer that implements the method 100. The temporally modulated illumination provides illumination for the subject that varies in intensity as function of time. For example, the temporally modulated illumination may have a periodically varying illumination intensity level such as a sinusoidal variation in illumination intensity level over time.

The overall acquisition time for each of the images may be defined by the frame rate of an imaging device of the imaging system. For example, some imaging devices may operate with a frame rate of 30 fps resulting in each frame being acquired over ~30 ms. Some other imaging devices may operate with a different frame rate. An increased frame rate (e.g., of more than 30 fps) achieved by certain imaging devices may reduce artefacts in acquired images caused by relative motion but may acquire less light due to the lower exposure time per frame (which may affect the quality of the image) and/or these imaging devices may be relatively more expensive and/or complicated to implement than some other imaging devices with a lower frame rate. Conversely, a lower frame rate (e.g., of less than 30 fps) achieved by certain imaging devices may increase artefacts in acquired images caused by relative motion but the increased exposure time per frame may provide an increased quality image compared with a higher frame rate imaging device.

Providing the delay between the acquisition start time for each subsequent image is less than the overall acquisition time for each image, the imaging system may operate with an effectively increased frame rate while also providing adequate image quality (due to the exposure time of each image still being sufficiently long to acquire enough light for the image). For example, if each image takes 30 ms to be acquired, the first image may start to be acquired at a time t=0 (zero) ms. The second image may start to be acquired at a time that is less than 30 ms after t=0 (e.g., at t=5 ms, or at another appropriate time). The third image may start to be acquired at a time that is less than 30 ms after t=0 (e.g., at t=10 ms, or at another appropriate time). Thus, each of the second and third images start to be acquired while the first image is being acquired. Further, the third image starts to be acquired while the second image is being acquired. In an example, if 3 (three) images are acquired within a timeframe of 40 ms (as per the above example), the effective frame rate is 3/40 ms=75 fps (i.e., instead of 30 fps without overlapping the acquisition of the first, second and third images). Thus, a higher frame rate may be achieved while ensuring that the exposure time is sufficiently long to achieve an adequate image quality.

As will be described in more detail below, the imaging system may be configured to acquire at least the first, second and third images with the time delay as described in block 102 to achieve the increased frame rate while also providing adequate image quality.

The method 100 further comprises, at block 104, determining modified pixel information (e.g., pixel intensity values) for constructing a modified image (referred to herein as an 'ambient-corrected image') of the subject. The modified pixel information is based on a difference between the received pixel information of the first, second and third images to reduce an effect of ambient lighting in the received pixel information. The modified pixel information is further based on a combination of the received pixel information to cancel out a spatial intensity modulation pattern apparent in each of the first, second and third images. The spatial intensity modulation pattern is due to a timing relationship between an imaging time period over which the imaging system acquires each image and a modulation time period of the temporally modulated illumination. In other similar words, block 104 determines an estimated intensity distribution (i.e., the 'modified pixel information') for an image (i.e., the 'modified image') of the subject, to reduce an effect of ambient lighting caused by a light source. Determining the estimated intensity distribution is based on a spatial intensity modulation pattern in each of the first, second and third images.

A spatial intensity modulation pattern may be observed in each of the first, second and third images. The spatial intensity modulation pattern may be the result of the temporally modulated illumination causing a variation in the illumination level over time while the image is being acquired (e.g., in some embodiments this may be due to a roller shutter effect causing different spatial portions of the imaging device detecting the varying illumination levels while scanning across these spatial portions). For example, a certain spatial portion of an imaging device may, at a certain time when the illumination level provided by the illumination unit is high, register a relatively high illumination level while another spatial portion of an imaging device may, at a later time in the same frame when the illumination level provided by the illumination unit is low, register a relatively low illumination level.

This means that the entire image may exhibit certain regions with a relatively higher illumination level than other regions and this may be considered to represent a 'spatial intensity modulation pattern'—an example of this pattern is described below. Depending on the relative timing (i.e., the 'timing relationship') of the image acquisition, the imaging acquisition rate and the modulation frequency of the temporally modulated illumination, the spatial intensity modulation pattern may vary between subsequent images. Thus, in some cases, the first, second and third images may each have a different spatial intensity modulation pattern. From this information, it may be possible to estimate the intensity distribution for the image (i.e., an ambient-corrected or ambient-compensated image constructed based on the first, second and third images) that reduces the effect of ambient lighting caused by a light source (e.g., a different light source to the illumination unit such as a lightbulb, daylight, etc). In other similar words, the spatial intensity modulation pattern is due to the timing relationship between the imaging time period over which the imaging system acquires each image and the modulation time period of the temporally modulated illumination. As mentioned in relation to block 104, the combination of the received pixel information may cancel out the spatial intensity modulation pattern apparent in each of the first, second and third images, while the difference between the received pixel information of the first, second and third images may reduce an effect of ambient lighting in the received pixel information.

Certain methods described herein (e.g., the method 100) may allow an ambient-corrected (or normalized) image to be obtained in a relatively short capture time, which may reduce artefacts from relative motion that may otherwise adversely affect the reduction of the effect of ambient lighting. The amount of light captured with each image may be sufficient to provide adequate image quality to facilitate the ambient light reduction, correction or normalization, which is described in more detail below.

In the case of ambient light reduction, normalization or correction using the temporally modulated illumination technique described above, the quality of the ambient light removal may be affected by the relative motion. According to certain embodiments described herein, a relative fast image acquisition time may be achieved, which may result in an ambient light reduction, correction or normalization that is robust to the relative motion with an image quality that may be useful for skin sensing applications.

Figure 2:
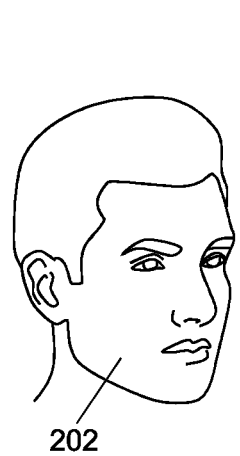
FIG. 2 is a schematic drawing of a system for improving imaging in certain settings according to an embodiment.
Figure 2:
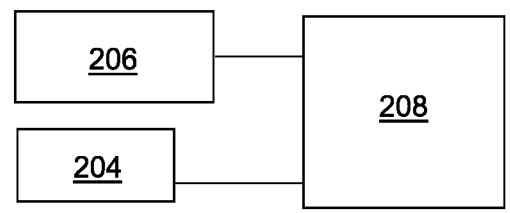

FIG. 2 shows an example system 200 for improving imaging according to certain embodiments. The system 200 may at least partially implement certain methods described herein such as method 100 above or method 600 below.

The system 200 is used by a subject 202 and comprises an imaging system 204 and an illumination unit 206. The imaging system 204 is used to acquire the images referred to in the method 100. The illumination unit 206 is used to provide the temporally modulated illumination. The imaging system 204 and/or the illumination unit 206 may be implemented by a user device such as described above. Thus, in some examples, separate user devices may comprise the imaging system 204 and the illumination unit 206 and, in other examples, the same user device may comprise the imaging system 204 and the illumination unit 206.

In some embodiments, the imaging system 204 comprises at least two imaging devices for capturing images or video (e.g., cameras in rolling shutter mode) capable of detecting a single or plurality of light sources interacting with the surface of the subject 202. The frame rates of the at least two imaging devices may be similar to each other. Further, in some embodiments, the imaging axes of the at least two imaging devices may be substantially collinear.

The system 200 further comprises a computer 208 (e.g., comprising processing circuitry implemented by a user device or a server or cloud-based service for implementing certain methods described herein). Thus, the computer 208 may be communicatively coupled to the imaging system 204 and the illumination unit 206 to send and/or receive information to/from these components. For example, the computer 208 may receive data corresponding to the first, second and third images from the imaging system 204. This data may be processed by the processing circuitry of the computer 208 and/or be stored in a memory (e.g., of the computer 208 or accessible to processing circuitry of the computer 208). In some embodiments, the computer 208 may control the operation of the imaging system 204 and/or the illumination unit 206. In some embodiments, the computer 208 comprises a controller for controlling illumination parameters (e.g., operating parameters for the illumination unit 206) and/or detection parameters (e.g., operating parameters for the imaging system 204) and storing and/or processing the captured images or videos.

Figure 3A:
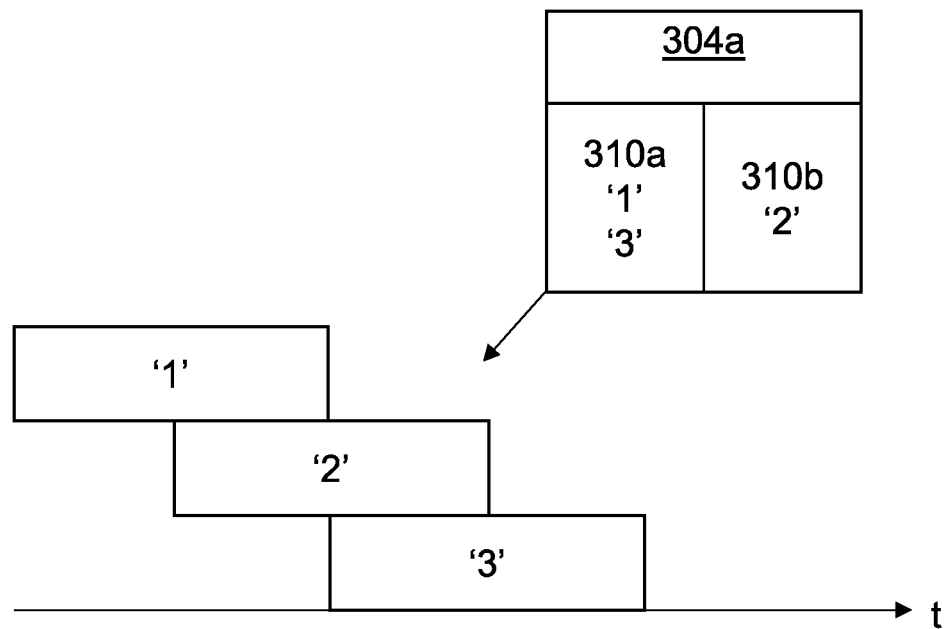
FIGS. 3a-b are schematic drawings of imaging systems according to two embodiments.
Figure 3B:
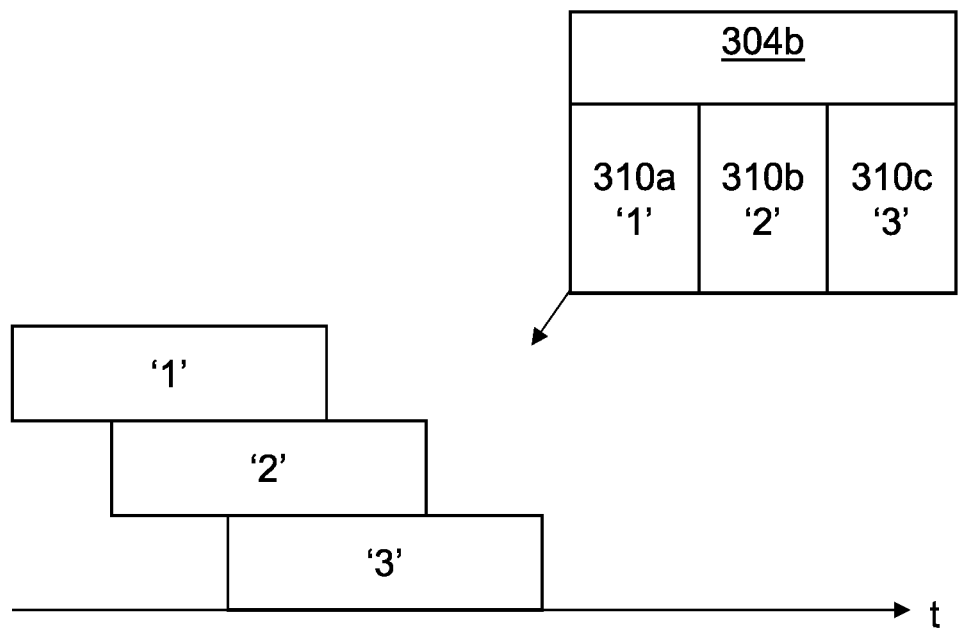

FIGS. 3*a-b* schematically depict two different imaging systems 304*a* and 304*b* (e.g., of the system 200 shown by FIG. 2) for acquiring the first, second and third images according to two embodiments.

The imaging system 304*a* of FIG. 3*a* comprises first and second imaging devices 310*a* and 310*b*. These two imaging devices 310*a-b* can be triggered to begin acquiring images that have a time delay between the images while still providing a time overlap between at least two of the first, second and third images. The acquisition timing of the first, second and third images (labeled '1', '2', and '3', respectively in the figure) is depicted by the timeline in FIG. 3*a*. At the start of acquisition, the first image '1' is obtained using the first imaging device 310*a*. After a time delay that is less than the overall acquisition time of the first image (e.g., see the 'length' of box '1' in FIG. 3*a*), the second image '2' is obtained using the second imaging device 310*b*. After another time delay that is less than the overall acquisition time of the second image (e.g., see the 'length' of box '2' in FIG. 3*a*), the third image '3' is obtained using the first imaging device 310*a* (i.e., after finishing the acquisition of the first image '1').

The use of two imaging devices 310*a*, 310*b* in the implementation described above may allow the first, second and third images to be acquired in less time than if using a single imaging device. Thus, the effective frame rate can be increased using the imaging system 304*a*. In this example, the start time for acquiring the second image '2' is at the half-way point during acquisition of the first image '1'. For example, if the acquisition time for the first image '1' is 30 ms, then acquisition of the second image '2' begins 15 ms after beginning the acquisition of the first image '2', and similarly for acquiring the third image '3' with respect to the second image '2'. This timing configuration may be different in other embodiments. For example, the second image '2' may be acquired at a different time delay relative to starting acquisition of the first image '1' (e.g., before or after the half-way point), and similarly for third image '3' with respect to the second image '1'.

The imaging system 304*b* of FIG. 3*b* can be implemented in a similar way to the imaging system 304*a* of FIG. 3*a*. However, the imaging system 304*b* comprises first, second and third imaging devices 310*a*, 310*b* and 310*c* for acquiring the first, second and third images, respectively. Thus, the third imaging device 310*c* can begin to acquire the third image '3' before first imaging device 310*a* has finished acquiring the first image '1'. Compared with the imaging system 304*a* of FIG. 3*a*, the imaging system 304*b* may provide a faster effective frame rate.

Thus, in some embodiments, the imaging system comprises at least two imaging devices for acquiring the first, second and third images. In some embodiments, the at least two imaging devices comprise imaging devices configured to operate in a rolling shutter mode (i.e., rolling shutter cameras). These imaging devices may be placed very close to each other similar to what can be found in some devices such as smartphones. In some embodiments, the at least two imaging devices comprise imaging devices configured to operate in a global shutter mode.

Further, in some embodiments, one of the imaging devices is used to acquire at least one of the first, second and third images and at least one other of the imaging devices is used to acquire at least one other of the first, second and third images.

Figure 4:
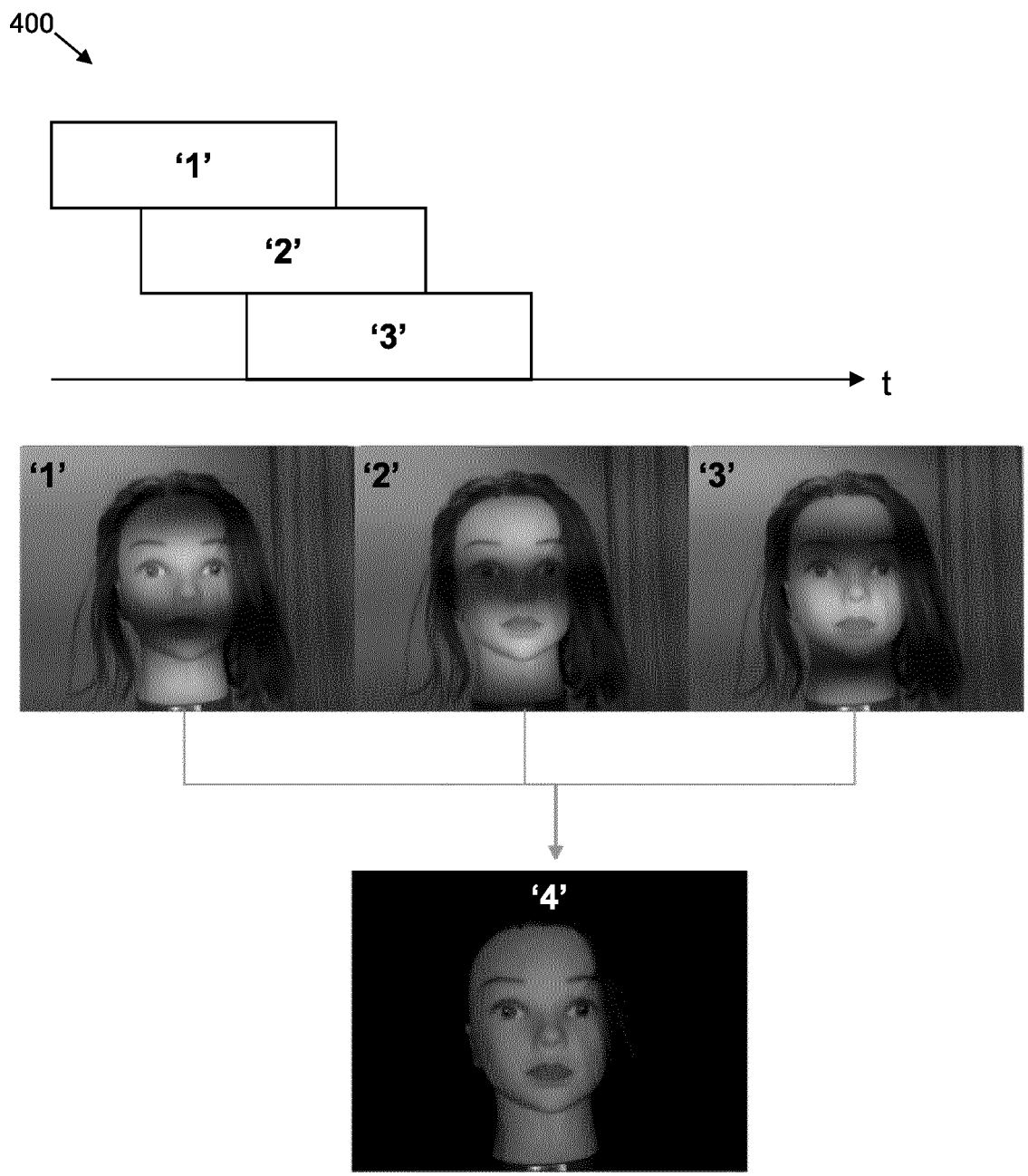
FIG. 4 is a schematic drawing of a system for implementing certain methods described herein according to an embodiment.

FIG. 4 schematically depicts a system for implementation of certain methods described herein based on implementing the imaging system 304*b* of FIG. 3*b* where first, second and third images '1', '2' and '3' are acquired with three imaging devices 310*a*, 310*b* and 310*c*. The first, second and third images shown in FIG. 4 feature the spatial intensity modulation pattern described above. Based on the data corresponding to these three images, the 'ambient-corrected' image '4' can be determined (e.g., in accordance with block 104 of the method 100).

As mentioned above, the determined modified pixel information is based on a difference between the received pixel information of the first, second and third images to reduce an effect of ambient lighting in the received pixel information. The determined modified pixel information is further based on a combination of the received pixel information to cancel out a spatial intensity modulation pattern apparent in each of the first, second and third images.

In some embodiments, the modified pixel information for constructing the modified image of the subject is determined by subtracting pixel information of different pair combinations of the first, second and third images to reduce the effect of ambient lighting in the received pixel information and combining the received pixel information to cancel out the spatial intensity modulation pattern apparent in each of the first, second and third images.

In some embodiments, the imaging system is configured to operate in a mode according to the timing relationship between the imaging time period over which the imaging system acquires each image and the modulation time period of the temporally modulated illumination. The mode may either be: a rolling shutter mode where the imaging time period of the imaging system is longer than the modulation time period; or a global shutter mode where the imaging time period is shorter than the modulation time period. In either mode, the spatial intensity modulation pattern may be observed in each of the acquired images.

Providing the phase shift between the spatial intensity modulation pattern in the three images is equal (e.g., 120 degrees for the above embodiment), it is possible to estimate the intensity of the ambient-corrected image, $M_{AC}$, according to the example formula:

$$M_{AC} = \frac{\sqrt{2}}{3}\{(I_1 - I_2)^2 + (I_2 - I_3)^2 + (I_1 - I_3)^2\}^{1/2},$$

where $I_1$ refers to the (pixel) intensity value in the first image, $I_2$ refers to the (pixel) intensity value in the second image and $I_3$ refers to the (pixel) intensity value in the third image. As indicated by the above formula, the ambient-correct image (i.e., the modified pixel information for constructing such an image) is determined based on the 'difference' between the received pixel information of the first, second and third images (i.e., $(I_1-I_2)$, etc.) and the 'combination' of the received pixel information (i.e., $(I_1-I_2)^2+(I_2-I_3)^2+(I_1-I_3)^2$). In some embodiments, each expression $(I_1-I_2)$, $(I_2-I_3)$ and $(I_1-I_3)$ refers to a 'pair combination'. Some embodiments described herein refer to at least one 'additional image' (in addition to the first, second and third images). Thus, the example formula may be modified according to how many images are acquired.

In some embodiments, the modulation time period of the temporally modulated illumination (i.e., 'illumination flicker') is around 15 ms (i.e., for a modulation frequency of 70 Hz). By triggering the capture of the images with a delay of 5 ms for the second imaging device and 10 ms for the third imaging device, the resulting spatial intensity modulation pattern in the captured first, second and third images may have a phase shift of 120 degrees.

Thus, in some embodiments, the time delay between the acquisition start times of the first, second and third images is based on the modulation time period of the temporally modulated illumination. For example, if the modulation time period is shorter than the above embodiment due to the illumination unit providing temporally modulation illumination at a frequency that is greater than 70 Hz, the time delay between the first, second and third images may be less than the above embodiment.

In some embodiments, the time delay between the acquisition start times (i.e., of the first, second, third images) corresponds to the modulation time period divided by the number of the images. Thus, in the above embodiment, the modulation time period is around 15 ms and three images are acquired. Thus, the time delay to use is around 5 ms for this embodiment.

In some embodiments, a modulation frequency of the temporally modulated illumination and/or a frame rate associated with the first, second and third images is configured such that a phase shift between the spatial intensity modulation patterns of the first, second and third images is the same. In other similar words, the modulation frequency and/or the frame rate of the imaging system may be configured such that the phase shift is the same between the first, second and third images.

In some embodiments, receiving the data (e.g., of block 102) further comprises receiving data corresponding to at least part of at least one additional image of the subject (e.g., a fourth, fifth, etc. image acquired by one of at least two imaging devices). The time delay between the acquisition start time of the first, second, third and at least one additional image is such that there is an overlap in time during acquisition of the first, second, third and the at least one additional image. Determining the modified pixel information (e.g., of block 104) is based on: a difference between the received pixel information of the first, second, third and at least one additional images to reduce an effect of ambient lighting in the received pixel information; and a combination of the received pixel information to cancel out a spatial intensity modulation pattern apparent in each of the first, second, third and at least one additional images. Some imaging devices may be configured to acquire more than three images (e.g., if such imaging systems are configured appropriately and/or if they comprise more than two or more than three imaging devices).

In some embodiments, the time delay between the acquisition start time of the first, second, third and at least one additional image is based on a modulation time period of the temporally modulated illumination. The time delay between the acquisition start time may correspond to the modulation time period divided by the number of the images. For example, if the imaging system is capable of acquiring a larger number of images than the above embodiments (e.g., at least four images), the time delay between the acquisition time of the first, second, third, fourth (or more) images may be less than in the above embodiments for the same modulation time period (i.e., 15 ms).

Figure 5A:
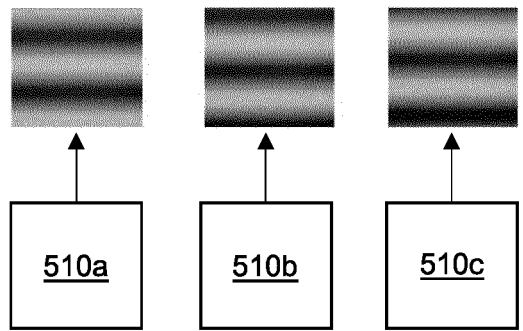
FIGS. 5a-b are schematic drawings of imaging systems according to two embodiments.
Figure 5B:
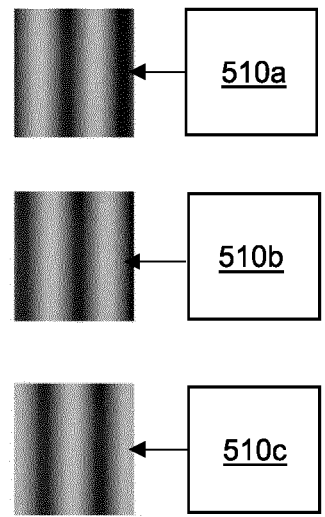

FIGS. 5*a*-*b* schematically depict possible orientations of the rolling shutter scanning direction implemented by the imaging devices 510*a*, 510*b*, 510*c* (e.g., similar to the imaging devices 310*a*, 310*b*, 310*c* of FIG. 3*b*). The rolling shutter scanning direction is the same for each imaging system such that the spatial intensity modulation pattern in each image 'scans' in the same direction (as shown in FIGS. 5*a*-*b*). FIG. 5*a* shows the three imaging devices 510*a*, 510*b*, 510*c* positioned at horizontally separated positions with the rolling shutter scanning direction being in the vertical direction. FIG. 5*b* shows the three imaging devices 510*a*, 510*b*, 510*c* positioned at vertically separated positions with the rolling shutter scanning direction being in the horizontal direction. In some embodiments, the imaging devices are aligned in the same (i.e., parallel) direction as the rolling shutter scanning direction. In some embodiments, the imaging devices are aligned in a perpendicular direction as the rolling shutter scanning direction.

In the case where the position of the imaging devices are in a different direction of the rolling shutter scanning direction, an adjustment in the time delay may be used such that the phase shift of the pattern corresponds to 120 degrees with respect to the targeted subject. In some embodiments, the scanning direction of the rolling shutter sensors is different for each sensor.

Figure 6:
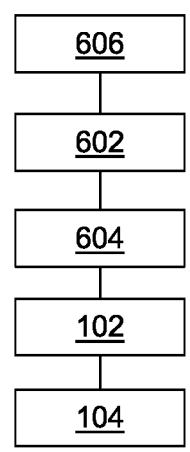
FIG. 6 refers to a method of improving imaging in certain settings according to an embodiment.

FIG. 6 shows a method 600 (e.g., a computer-implemented method) of improving imaging in certain settings. The method 600 may be implemented by a computer such as a user device, or a server or cloud-based service (e.g., communicatively coupled to the user device). The method 600 comprises blocks 102 and 104 of the method 100. Certain blocks of the method 600 may be omitted and/or the blocks shown by FIG. 6 may be implemented in a different order to the depicted order. For ease, reference is made to the system 200 of FIG. 2 when describing the implementation of the method 600.

In some embodiments, the method 600 further comprises, at block 602, causing the imaging system 204 to acquire the first, second and third images. In some embodiments, more than three images may be acquired, in which case the imaging system 204 may be caused to acquire the first, second, third and the at least one additional image.

In some embodiments, the method 600 comprises, at block 604 and before determining the modified pixel information, identifying whether or not a position of the subject within the first, second and third images is the same. Where a difference in the subject's position in at least one of the images compared with at least one other of the images exceeds a threshold (e.g., a threshold number of pixels for a certain feature of the image to be shifted between the images), block 604 of the method 600 comprises implementing an image shift operation in at least one of the first, second and third images so that the position of the subject in each of the first, second and third images is the same. For example, due to the distance between the imaging devices and/or due to relative motion between the subject and the imaging system, an image shift may need to be used to realign the images properly before ambient light correction (e.g., at block 104) is performed.

However, in some embodiments, to avoid the image shift issue due to the distance between the imaging devices, a beam splitter or other optical arrangement (not shown) may be used to image exactly the same image but with different imaging devices configured to receive the image using the same optical arrangement.

In some embodiments, the method 600 comprises, at block 606, receiving an indication of a modulation parameter (e.g., a modulation frequency or modulation period) of the temporally modulated illumination; determining an operating parameter (e.g., a frame rate, image acquisition start time, etc.) for the imaging system 204 based on the indication; and causing the imaging system 204 to operate according to the operating parameter. For example, the system 200 may determine or receive an indication of the modulation frequency of the temporally modulated illumination and adjust the frame rate and the time delay between the imaging devices of the imaging system 204 accordingly.

Figure 7:
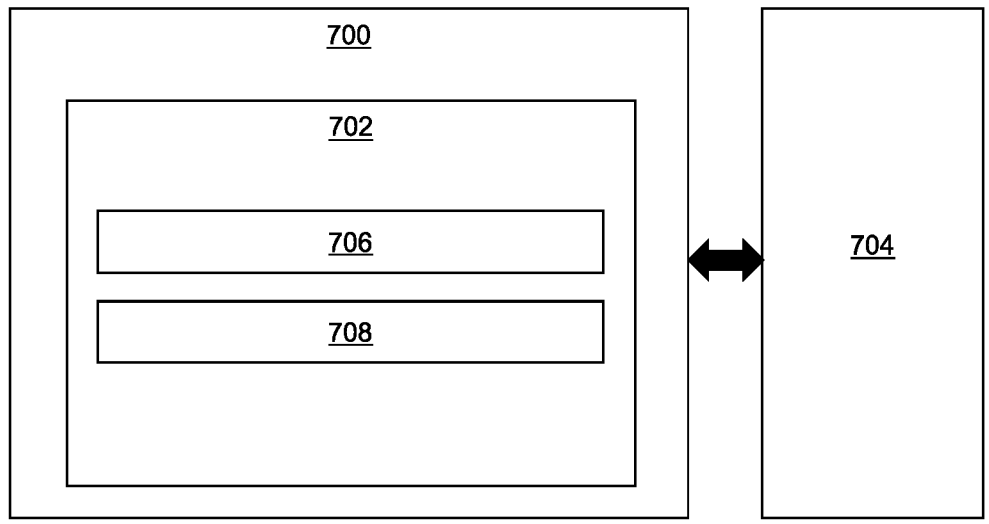
FIG. 7 is a schematic drawing of a machine-readable medium for improving imaging in certain settings according to an embodiment.

FIG. 7 schematically depicts a tangible machine-readable medium 700 storing instructions 702 which, when executed by at least one processor 704, cause the at least one processor 704 to implement certain methods described herein, for example, the method 100 or 600.

In this embodiment, the instructions 702 comprise instructions 706 to cause the at least one processor 704 to implement block 102 of the method 100. The instructions 702 further comprise instructions 708 to cause the at least one processor 704 to implement block 104 of the method 100.

Figure 8:
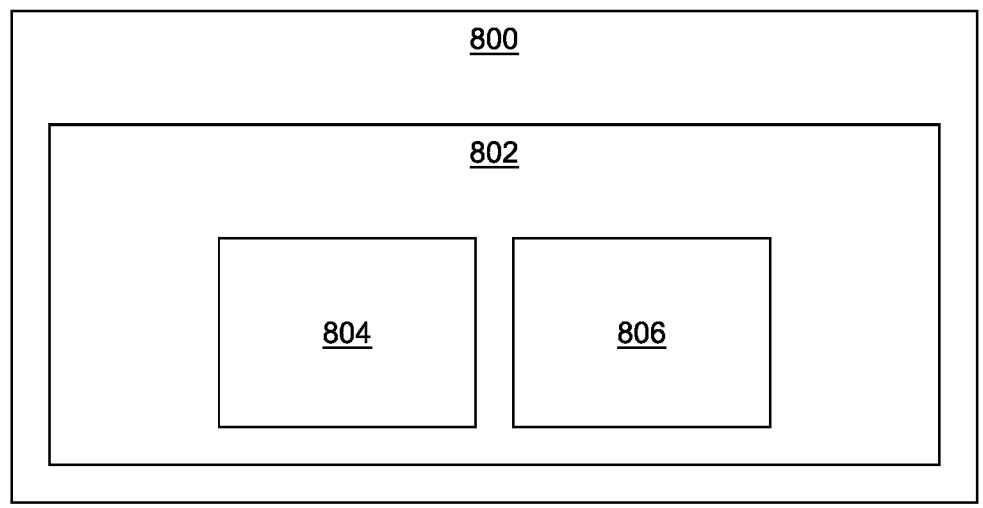
FIG. 8 is a schematic drawing of an apparatus for improving imaging in certain settings according to an embodiment.

FIG. 8 shows an apparatus 800, which may be used for implementing certain methods described herein such as the method 100 and/or the method 600. The apparatus 800 may comprise modules with functionality corresponding to certain features described in relation to the system 200 of FIG. 2 such as the computer 208 thereof.

The apparatus 800 comprises processing circuitry 802. The processing circuitry 802 comprises a receiving module 804 configured to receive pixel information corresponding to at least part of a first, second and third image, acquired by an imaging system, of a subject illuminated by temporally modulated illumination. A time delay between an acquisition start time of the first, second and third images is such that there is an overlap in time during acquisition of the first, second and third images.

The processing circuitry 802 further comprises a determining module 806 configured to determine modified pixel information for constructing a modified image of the subject based on: a difference between the received pixel information of the first, second and third images to reduce an effect of ambient lighting in the received pixel information; and a combination of the received pixel information to cancel out a spatial intensity modulation pattern apparent in each of the first, second and third images. The spatial intensity modulation pattern is due to a timing relationship between an imaging time period over which the imaging system acquires each image and a modulation time period of the temporally modulated illumination.

In some embodiments, the apparatus 800 further comprises the imaging system (e.g., the imaging system 204 of FIG. 2) for acquiring the pixel information corresponding to at least part of the first, second and third images.

In some embodiments, the apparatus 800 further comprises an illumination unit (e.g., the illumination unit 206 of FIG. 2) for providing the temporally modulated illumination.

In some embodiments, the imaging system 204, 304 comprises at least two imaging devices (e.g., imaging devices 310a, 310b, 310c of FIG. 3b), wherein a scanning direction for a rolling shutter implemented by the at least two imaging devices is the same.

In some embodiments, the imaging system 304 comprises at least two imaging devices 310a, 310b, 310c.

In some embodiments, the imaging system 304 is configured to operate in a mode according to the timing relationship between the imaging time period over which the imaging system acquires each image and the modulation time period of the temporally modulated illumination. The mode may be either: a rolling shutter mode where the imaging time period of the imaging system is longer than the modulation time period; or a global shutter mode where the imaging time period is shorter than the modulation time period.

In some cases, any of the modules described above (e.g., the receiving module 804 and/or the determining module 806) may comprise at least one dedicated processor (e.g., an application specific integrated circuit (ASIC) and/or field programmable gate array (FPGA), etc) for implementing the functionality of the module.

In some cases, the module above (e.g., the receiving module 804 and/or the determining module 806) may comprise at least one processor for implementing instructions which cause the at least one processor to implement the functionality of the module described above. In such examples, the instructions may be stored in a machine-readable medium (not shown) accessible to the at least one processor. In some examples, the module itself comprises the machine-readable medium. In some examples, the machine-readable medium may be separate to the module itself (e.g., the at least one processor of the module may be provided in communication with the machine readable medium to access the instructions stored therein).

While the invention has been illustrated and described in detail in the drawings and foregoing description, such illustration and description are to be considered illustrative or exemplary and not restrictive; the invention is not limited to the disclosed embodiments.

One or more features described in one embodiment may be combined with or replace features described in another embodiment. For example, the methods 100, 600 of FIG. 1 or 6 may be modified based on features described in relation to the system 200 (with reference to FIGS. 2 to 5), machine-readable medium 700 and/or the apparatus 800, and vice versa.

This disclosure includes subject-matter defined by the following numbered paragraphs:

Paragraph 1. A computer-implemented method comprising:
  receiving data corresponding to at least part of a first, second and third image of a subject illuminated by temporally modulated illumination, wherein a time delay between an acquisition start time of the first, second and third images is such that there is an overlap in time during acquisition of the first, second and third images; and determining, based on a spatial intensity modulation pattern in each of the first, second and third images, an estimated intensity distribution for an image of the subject, to reduce an effect of ambient lighting caused by a light source.

Paragraph 2. The method of paragraph 1, wherein the time delay between the acquisition start times of the first, second and third images is based on a modulation time period of the temporally modulated illumination.

Paragraph 3. The method of paragraph 2, wherein the time delay between the acquisition start times corresponds to the modulation time period divided by the number of the images.

Paragraph 4. The method of any preceding paragraph, wherein at least two imaging devices of an imaging system are used to acquire the images.

Paragraph 5. The method of paragraph 4, wherein one of the imaging devices is used to acquire at least one of the first, second and third images and at least one other of the imaging devices is used to acquire at least one other of the first, second and third images.

Paragraph 6. The method of paragraph 4 or 5, further comprising causing the imaging system to acquire the first, second and third images.

Paragraph 7. The method of any one of paragraphs 4 to 6, comprising: receiving an indication of a modulation parameter of the temporally modulation illumination; determining an operating parameter for the imaging system based on the indication; and causing the imaging system to operate according to the operating parameter.

Paragraph 8. The method of any preceding paragraph, wherein a modulation frequency of the temporally modulated illumination and/or a frame rate associated with the first, second and third images is configured such that a phase shift between the spatial intensity modulation patterns of the first, second and third images is the same.

Paragraph 9. The method of any preceding paragraph, comprising, before determining the estimated intensity distribution, identifying whether or not a position of the subject within the first, second and third images is the same and, where a difference in the subject's position in at least one of the images compared with at least one other of the images exceeds a threshold, implementing an image shift operation in at least one of the first, second and third images so that the position of the subject in each of the first, second and third images is the same.

Paragraph 10. The method of any preceding paragraph, wherein receiving the data further comprises receiving data corresponding to at least part of at least one additional image of the subject, wherein the time delay between the acquisition start time of the first, second, third and at least one additional image is such that there is an overlap in time during acquisition of the first, second, third and the at least one additional image, and wherein determining the estimated intensity distribution is based on the spatial intensity modulation pattern in each of the first, second, third and at least one additional image.

Paragraph 11. The method of paragraph 10, wherein the time delay between the acquisition start time of the first, second, third and at least one additional image is based on a modulation time period of the temporally modulated illumination, and wherein the time delay between the acquisition start time corresponds to the modulation time period divided by the number of the images.

Paragraph 12. A tangible machine-readable medium storing instructions which, when executed by at least one processor, cause the at least one processor to implement the method according to any preceding paragraph.

Paragraph 13. Apparatus comprising processing circuitry, the processing circuitry comprising:
  a receiving module to receive data corresponding to at least part of a first, second and third image of a subject illuminated by temporally modulated illumination, wherein a time delay between an acquisition start time of the first, second and third images is such that there is an overlap in time during acquisition of the first, second and third images; and
  a determining module to determine, based on a spatial intensity modulation pattern in each of the first, second and third images, an estimated intensity distribution for an image of the subject, to reduce an effect of ambient lighting caused by a light sources.

Paragraph 14. The apparatus of paragraph 13, further comprising: an imaging system for acquiring the data corresponding to at least part of the first, second and third images; and/or an illumination unit for providing the temporally modulated illumination.

Paragraph 15. The apparatus of paragraph 14, wherein the imaging system comprises at least two imaging devices, wherein a scanning direction for a rolling shutter implemented by the at least two imaging devices is the same.

Embodiments in the present disclosure can be provided as methods, systems or as a combination of machine-readable instructions and processing circuitry. Such machine-readable instructions may be included on a non-transitory machine (for example, computer) readable storage medium (including but not limited to disc storage, CD-ROM, optical storage, etc.) having computer readable program codes therein or thereon.

The present disclosure is described with reference to flow charts and block diagrams of the method, devices and systems according to embodiments of the present disclosure. Although the flow charts described above show a specific order of execution, the order of execution may differ from that which is depicted. Blocks described in relation to one flow chart may be combined with those of another flow chart. It shall be understood that each block in the flow charts and/or block diagrams, as well as combinations of the blocks in the flow charts and/or block diagrams can be realized by machine readable instructions.

The machine readable instructions may, for example, be executed by a general purpose computer, a special purpose computer, an embedded processor or processors of other programmable data processing devices to realize the functions described in the description and diagrams. In particular, a processor or processing circuitry, or a module thereof, may execute the machine readable instructions. Thus functional modules of the system 200 and/or the apparatus 800 (for example, receiving module 806 and/or the determining module 808) and other devices described herein may be implemented by a processor executing machine readable instructions stored in a memory, or a processor operating in accordance with instructions embedded in logic circuitry. The term 'processor' is to be interpreted broadly to include a CPU, processing unit, ASIC, logic unit, or programmable gate array etc. The methods and functional modules may all be performed by a single processor or divided amongst several processors.

Such machine readable instructions may also be stored in a computer readable storage that can guide the computer or other programmable data processing devices to operate in a specific mode.

Such machine readable instructions may also be loaded onto a computer or other programmable data processing devices, so that the computer or other programmable data processing devices perform a series of operations to produce computer-implemented processing, thus the instructions executed on the computer or other programmable devices realize functions specified by block(s) in the flow charts and/or in the block diagrams.

Further, the teachings herein may be implemented in the form of a computer program product, the computer program product being stored in a storage medium and comprising a plurality of instructions for making a computer device implement the methods recited in the embodiments of the present disclosure.

Elements or steps described in relation to one embodiment may be combined with or replaced by elements or steps described in relation to another embodiment. Other variations to the disclosed embodiments can be understood and effected by those skilled in the art in practising the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computer-implemented method comprising:
receiving pixel intensity values corresponding to at least part of a first, second and third image, acquired by an imaging system, of a subject illuminated by temporally modulated illumination, wherein a time delay between an acquisition start time of the first, second and third images is such that there is an overlap in time during acquisition of at least two of the first, second and third images, wherein:
the time delay between the acquisition start times of the first, second and third images is based on a modulation time period of the temporally modulated illumination; and
the time delay between the acquisition start times corresponds to the modulation time period divided by the number of the images such that a timing relationship between an imaging time period over which the imaging system acquires each image and the modulation time period of the temporally modulated illumination is such that a different spatial intensity modulation pattern is registered in each of the first, second and third images; and
determining modified pixel intensity values for constructing a modified image of the subject based on:
a difference between the received pixel intensity values of each different pair combination of the first, second and third images to determine pixel intensity values for each different pair combination, wherein the difference reduces an effect of ambient lighting present when each of the first, second and third images were acquired; and
a combination of the determined pixel intensity values for each different pair combination to cancel out the spatial intensity modulation pattern apparent in each of the first, second and third images.

2. The method of claim 1, wherein the modified pixel intensity values for constructing the modified image of the subject are determined based on:
subtracting pixel intensity values of corresponding pixels from each different pair combination of the first, second and third images to produce a resulting pixel intensity value for each corresponding pixel of each different pair combination, wherein the subtraction reduces the effect of ambient lighting present when each of the first, second and third images were acquired; and
squaring the resulting pixel intensity value of each different pair combination and summing each squared resulting pixel intensity value to cancel out the spatial intensity modulation pattern apparent in each of the first, second and third images.

3. The method of claim 1, wherein a phase shift of the spatial intensity modulation pattern between the first, second and third images is equal, and wherein the modified pixel intensity values for constructing the modified image, MAC, of the subject are determined based on a formula:

$$M_{AC} = \frac{\sqrt{2}}{3}((I_1 - I_2)^2 + (I_2 - I_3)^2 + (I_1 - I_3)^2)^{1/2},$$

where $I_1$ refers to the pixel intensity values in the first image, $I_2$ refers to the pixel intensity values in the second image and $I_3$ refers to the pixel intensity values in the third image.

4. The method of claim 1, wherein the imaging system comprises at least two imaging devices for acquiring the first, second and third images.

5. The method of claim 4, wherein one of the imaging devices is used to acquire at least one of the first, second and third images and at least one other of the imaging devices is used to acquire at least one other of the first, second and third images.

6. The method of claim 4, further comprising causing the imaging system to acquire the first, second and third images.

7. The method of claim 4, comprising:
receiving an indication of a modulation parameter of the temporally modulation illumination;
determining an operating parameter for the imaging system based on the indication; and causing the imaging system to operate according to the operating parameter.

8. The method of claim 1, wherein a modulation frequency of the temporally modulated illumination and/or a frame rate associated with the first, second and third images is configured such that a phase shift between the spatial intensity modulation patterns of the first, second and third images is the same.

9. The method of claim 1, comprising, before determining the modified pixel intensity values, identifying whether or not a position of the subject within the first, second and third images is the same and, where a difference in the subject's position in at least one of the images compared with at least one other of the images exceeds a threshold, implementing an image shift operation in at least one of the first, second and third images so that the position of the subject in each of the first, second and third images is the same.

10. The method of claim 1, wherein the imaging system is configured to operate in a mode according to the timing relationship between the imaging time period over which the imaging system acquires each image and the modulation time period of the temporally modulated illumination, wherein the mode is:
a rolling shutter mode where the imaging time period of the imaging system is longer than the modulation time period; or
a global shutter mode where the imaging time period is shorter than the modulation time period.

11. The method of claim 1, wherein receiving the data further comprises receiving pixel intensity values corresponding to at least part of at least one additional image of the subject, wherein the time delay between the acquisition start time of the first, second, third and at least one additional image is such that there is an overlap in time during acquisition of at least two of the first, second, third and the at least one additional image, wherein:
the time delay between the acquisition start times of the first, second, third and at least one additional images is based on the modulation time period of the temporally modulated illumination; and
the time delay between the acquisition start times corresponds to the modulation time period divided by the number of the images such that the timing relationship between the imaging time period over which the imaging system acquires each image and the modulation time period of the temporally modulated illumination is such that a different spatial intensity modulation pattern is registered in each of the first, second, third and at least one additional images, and wherein the modified pixel intensity values are determined based on:
a difference between the received pixel intensity values of each different pair combination of the first, second, third and at least one additional images to determine pixel intensity values for each different pair combination, wherein the difference reduces an effect of ambient lighting present when each of the first, second, third and at least one additional images were acquired; and
a combination of the determined pixel intensity values for each different pair combination to cancel out the spatial intensity modulation pattern apparent in each of the first, second, third and at least one additional images.

12. A tangible machine-readable medium storing instructions which, when executed by at least one processor, cause the at least one processor to implement the method according to claim 1.

13. Apparatus comprising processing circuitry, the processing circuitry comprising:
a receiving module configured to receive pixel intensity values corresponding to at least part of a first, second and third image, acquired by an imaging system, of a subject illuminated by temporally modulated illumination, wherein a time delay between an acquisition start time of the first, second and third images is such that there is an overlap in time during acquisition of at least two of the first, second and third images, wherein:
the time delay between the acquisition start times of the first, second and third images is based on a modulation time period of the temporally modulated illumination; and
the time delay between the acquisition start times corresponds to the modulation time period divided by the number of the images such that a timing relationship between an imaging time period over which the imaging system acquires each image and the modulation time period of the temporally modulated illumination is such that a different spatial intensity modulation pattern is registered in each of the first, second and third images; and
a determining module configured to determine modified pixel intensity values for constructing a modified image of the subject based on:
a difference between the received pixel intensity values of each different pair combination of the first, second and third images to determine pixel intensity values for each different pair combination, wherein the difference reduces an effect of ambient lighting present when each of the first, second and third images were acquired; and
a combination of the determined pixel intensity values for each different pair combination to cancel out the spatial intensity modulation pattern apparent in each of the first, second and third images.

14. The apparatus of claim 13, further comprising: the imaging system for acquiring the pixel intensity values corresponding to at least part of the first, second and third images; and/or an illumination unit for providing the temporally modulated illumination.

15. The apparatus of claim 13, wherein the imaging system comprises at least two imaging devices, and wherein the imaging system is configured to operate in a mode according to the timing relationship between the imaging time period over which the imaging system acquires each image and the modulation time period of the temporally modulated illumination, wherein the mode is:
  a rolling shutter mode where the imaging time period of the imaging system is longer than the modulation time period; or
  a global shutter mode where the imaging time period is shorter than the modulation time period.

* * * * *